(12) United States Patent
Barbreau et al.

(10) Patent No.: US 8,889,368 B2
(45) Date of Patent: Nov. 18, 2014

(54) USE OF FERROFLUIDS FOR PHENOTYPING BLOOD AND RELATED APPLICATIONS

(75) Inventors: Yves Barbreau, Mouvaux (FR); Olivier Boulet, Sailly Labourse (FR); Arnaud Boulet, Arras (FR); Alexis Delanoe, La Madeleine (FR); Laurence Fauconnier, Villeneuve d'Ascq (FR); Jean-Marc Pelosin, Lambersart (FR); Laurent Soufflet, Saint Amand les Eaux (FR)

(73) Assignee: Diagast, Loos (FR)

( * ) Notice: Subject to any disclaimer, the term of this patent is extended or adjusted under 35 U.S.C. 154(b) by 2482 days.

(21) Appl. No.: 11/579,383

(22) PCT Filed: May 3, 2005

(86) PCT No.: PCT/FR2005/001101
§ 371 (c)(1),
(2), (4) Date: Sep. 23, 2010

(87) PCT Pub. No.: WO2005/121805
PCT Pub. Date: Dec. 22, 2005

(65) Prior Publication Data
US 2011/0207151 A1    Aug. 25, 2011

(30) Foreign Application Priority Data
May 5, 2004   (FR) .................................... 04 04853

(51) Int. Cl.
*G01N 33/00*   (2006.01)
*G01N 33/543*   (2006.01)
*G01N 33/80*   (2006.01)

(52) U.S. Cl.
CPC .......... *G01N 33/54326* (2013.01); *G01N 33/80* (2013.01); *G01N 33/54346* (2013.01)

USPC ........................................................ 435/7.25

(58) Field of Classification Search
None
See application file for complete search history.

(56) References Cited

U.S. PATENT DOCUMENTS

| 4,329,241 | A | * | 5/1982 | Massart ..................... 252/62.52 |
| 5,318,914 | A | | 6/1994 | Matte et al. |
| 8,093,067 | B2 | * | 1/2012 | Barbreau et al. ............. 436/526 |
| 2004/0063163 | A1 | | 4/2004 | Buffiere et al. |
| 2004/0063218 | A1 | | 4/2004 | Buffiere et al. |

FOREIGN PATENT DOCUMENTS

| EP | 0 194 212 A1 | 9/1986 | |
| EP | 0230768 | * 12/1986 | ............... B03C 1/00 |
| EP | 0 230 768 | * 5/1987 | ............... B03C 1/00 |
| EP | 0 230 768 A1 | 8/1987 | |
| EP | 0 348 191 A1 | 12/1989 | |
| EP | 0 351 857 A2 | 1/1990 | |
| EP | 0 755 719 A2 | 1/1997 | |
| WO | WO 98/02752 A1 | 1/1998 | |
| WO | WO 02/40159 A2 | 5/2002 | |

* cited by examiner

*Primary Examiner* — Ann Lam
(74) *Attorney, Agent, or Firm* — Blakely Sokoloff Taylor & Zafman

(57) ABSTRACT

The invention relates to a method for phenotyping blood and/or performing an irregular agglutinin test and/or for determination of compatibility of a donor and receiver, using an aqueous solution of ferrofluid, obtained from a mixture of polyoxoanions of Fe(III) and at least one metal M(II) of oxidation state II. The invention further relates to a kit for carrying out said procedure.

45 Claims, No Drawings

USE OF FERROFLUIDS FOR PHENOTYPING BLOOD AND RELATED APPLICATIONS

This is a non-provisional application claiming the benefit of International application number PCT/FR2005/001101 filed May 3, 2005.

The present invention relates to a method of phenotyping blood and/or performing an irregular agglutinin test and/or for determining the compatibility of a donor and recipient, using an aqueous solution of ferrofluid obtained from a mixture of polyoxoanions of Fe(III) and at least one M(II) metal of oxidation state II. The invention further relates to a device and a kit for carrying out said method.

Blood transfusion today consists of intravenously administering preparations of concentrated red blood cells (globular concentrates) obtained from donated blood.

During a blood transfusion, the main risk is related to the possibility of bringing together an antibody and its blood-group antigen in the body of the recipient (the person transfused). Indeed, on the surface of erythrocytes, also called red blood cells or red blood corpuscles, are found erythrocyte membrane antigens, in particular blood group (or system) antigens, capable of being recognized by the immune system and triggering an immune response.

The red blood cells from the donor are known to be compatible with the blood of the recipient if the recipient does not have circulating antibodies directed against an erythrocyte antigen of the donor.

Among the entirety of the antigenic variants of erythrocyte membrane antigens that constitute the blood groups, more than twenty erythrocyte antigen systems have been identified to date in man: the ABO system with antigens A or B, the Rhesus system with antigens D, E or e and C or c, the Kell system with antigens K or k, Duffy (Fy a, Fy b), Kidd (Jka, Jkb) or still other systems less frequently used in practice such as MNS, Lewis, etc. Individuals with the same association of erythrocyte antigens belong to the same blood group. Blood groups are all the more complex and numerous if several antigen systems are used.

Apart from pathological situations, such as in the ease of autoimmune disease, an individual's serum can contain two types of antibodies directed against erythrocyte antigens:

(i) so-called "regular" antibodies directed against the antigens of the ABO system (for example, anti-A antibody in a group B individual). These are IgM-type immunoglobulins which are able to agglutinate red blood cells in vitro. This phenomenon is put to use to determine the ABO group of an individual by the Beth-Vincent and Simonin tests, the Beth-Vincent test making it possible to determine the antigens carried by the red blood cells (antigen phenotype) and the Simonin test making it possible to carry out a complementary study, that is to say, to determine the circulating anti-A and/or anti-B antibodies present in the individual's serum.

In the Beth-Vincent test, the individual's red blood cells are placed in the presence of test sera, or test antibodies, each having a specific type of antibody directed against an antigen of the ABO system. It is thus a test of the agglutination of the red blood cells with the test sera.

In the Simonin test, also called a counter-test, the individual's serum, containing the circulating antibodies, is placed in the presence of test red blood cells, or test erythrocytes, each belonging to a specific antigen group of the ABO system. It is thus a test of the agglutination of the serum with the test red blood cells:

(ii) so-called "irregular" (or "immune") antibodies whose presence in the serum or plasma is optional and which are directed against antigens of the non-ABO systems. This generally involves IgG, appearing during antigen stimulation by foreign red blood cells, for example following an immunization against one or more antigens during a blood transfusion or during pregnancy by a maternal immune reaction directed against fetal erythrocyte antigens not belonging to the maternal blood group, in particular during childbirth.

The search for these so-called irregular antibodies is called the irregular agglutinin test. This test is used to detect the presence or absence of IgG directed against various erythrocyte antigens in an individual's blood. In this test, evidence is sought for the binding of these IgG on test red blood cells whose antigens are known. The test proceeds in parallel on many types of red blood cells, the comparison of the results making it possible to deduce the IgG present.

The risk is higher for the most immunogenic antigens such as Rhesus D but also for the other Rhesus (E>c>e>C), Kell (K), Duffy (Fy a, Fy b), Kidd (Jka, Jkb), etc.

In practice, all these antigens cannot be taken into account during a transfusion or else the right blood group would never be available at the right moment, in addition to the fact than certain antigen associations are very rare. Standard transfusions only take into account the group in the ABO system plus Rhesus D (Rh+ or Rh−). In situations at risk of the appearance of irregular agglutinin, a certain number of other systems are taken into account, in particular Rhesus C and E and Kell, and other systems as well. It then becomes a question for these high-risk situations of respecting the compatibility of the donor's blood group with that of the recipient's blood by taking into account the presence or the risk of the appearance of these irregular agglutinins.

Thus, in a receiving patient carrying irregular anti-erythrocyte antibodies or in a high-risk situation such as, in particular, among multiply transfused patients who do not have an irregular anti-erythrocyte antibody and among pregnant woman, it is essential to select the units of erythrocyte concentrates which will be transfused in such a way that the donor's red blood cells will have had eliminated the antigens against which the antibodies of the recipient are directed or likely to appear. This proof of compatibility is obligatory among these patients and in a preventive manner among all recipients before the administration of erythrocyte concentrates by carrying out a test of direct compatibility with the red blood corpuscles of the donor in the presence of the serum or plasma of the recipient. No agglutination and/or lysis reaction in the techniques used for the irregular agglutinin test must be observed.

In clinical transfusion practice, erythrocyte phenotyping, which corresponds to the search for and the identification of blood-group antigens on the surface of red blood corpuscles (with the particular exception of the ABO system in which, in addition, the presence of corresponding regular antibodies is sought) involves the recipient as well as the donor.

At the level of the recipient and the donor, three levels of erythrocyte phenotyping exist in order to make compatible erythrocyte concentrates available for the recipient as a function of the situations at risk:

determination of the ABO group phenotype (or ABO group) and standard Rhesus (presence or absence of the D antigen);

determination of the Rhesus Kell phenotype (presence or absence of the C, F, e, c and K antigens); and the determination of the extended (or broad) phenotype (presence or absence of the Duffy system antigens Fy a and Fy b, the Kidd system antigens Jk a and Jk b, and the MNSs system antigens S and s); other antigens may be sought in addition according to the nature of the risk and/or of the irregular antibodies revealed in the serum of the recipient.

The techniques usually used, implemented to seek out and identify the presence or absence of blood-group antigens on the surface of donor and/or recipient erythrocytes, or targeting the search for and identification of the presence or absence of anti-antigen blood-group antibodies, regular (for the ABO group) or irregular within the framework of the irregular agglutinin test in the scrum or plasma of the donor and/or recipient, are well-known to those skilled in the art and will not be described here.

For phenotyping, they generally consist of an investigation using test sera containing the antibodies suitable to the presence or the absence of the antigen sought. Preferably, the antibodies contained in these test sera are agglutinating in nature (IgM or IgA), which makes it possible to obtain total or partial agglutination of the erythrocytes to be phenotyped when they carry the antigen corresponding to the antibody present in the test serum. Nevertheless, it is possible to use non-agglutinating test antibodies (IgG-type), the agglutination being initiated by means of an anti-immunoglobulin (the so-called indirect Coombs technique) in which the presence of non-agglutinating test antibodies bound to the red blood cell are visualized by means of an anti-immunoglobulin bound to a solid phase. The reading of the agglutination or of the red blood cells sensitized with the test antibodies bound to the solid phase via anti-immunoglobulin (so-called immunoadhesion technique) can be accomplished with the naked eye or by means of suitable reader.

For the search for and the identification of, in the patient's serum or plasma sample to be tested, anti-antigen blood-group antibodies, regular for ABO group or irregular within the framework of the irregular agglutinin test, the patient's serum or plasma is generally placed in the presence of test erythrocytes (also called test red blood corpuscles or test red blood cells) of known antigenicity in a certain number of blood-group systems (ABO, Rhesus, Kell, Duffy, Kidd, MNSs, etc.). For the irregular agglutinin test, for which the antibodies likely to be present are often of the non-agglutinating type, the techniques used are of the indirect Coombs type by agglutination by means of an anti-immunoglobulin or immunoadhesion on a solid phase coated with an anti-immunoglobulin.

For the irregular agglutinin test, in a first step a so-called screening red blood cell panel is used (two or three red blood cells of different groups chosen in order to contain the maximum amount of antigens), which makes it possible to detect (but not to identify) the presence or absence of irregular antibodies. When the screening is positive, the identification of the specificity of the irregular antibody or antibodies present is then carried out by means of at least one so-called identification red blood cell panel containing in general 10 red blood cells of various phenotypes in the large majority of the known blood group systems.

It can also be noted that during the compatibility test in which the red blood corpuscles of the donor are placed in the presence of the serum of the recipient, a first step of centrifugation is generally carried out in order to observe the possible presence of agglutination related to the presence in the recipient's serum of antibodies agglutinating the red blood cells of the donor (ABO incompatibility or IgM or IgA irregular antibodies), this first step being followed, if not by agglutination, by a search for antibodies by means of an anti-immunoglobulin (Coombs indirect anti-globulin technique).

There are a large number of variants of the techniques used for phenotyping or for the irregular agglutinin test in the field of blood transfusion; these techniques can be manual, on an opaline plate, in a test tube or a microplate well, or completely automated using an system that distributes the sample and the reagent, a shaker, an incubator and an automatic reader whose programs are adapted to the techniques implemented.

Among the techniques used, techniques can be cited for which the presence of anti-antigen blood-group antibodies or blood-group antigens is based on the demonstration of an agglutination of red blood cells after centrifugation using a transparent filtration mini-column ("Sephadex®" or microbead gel) whose upper flared section is used as an incubation chamber and for which the filtering threshold chosen for the column prevents red blood corpuscles agglutinated after centrifugation to pass through the column (sec in particular patent EP 0 194 212 or patent EP 0 755 719).

Techniques can also be cited for which the phenotyping or the irregular agglutinin test is based on the demonstration of red blood cells sensitized with an antibody after centrifugation and then immunoadhesion using a separation barrier comprised of a gel or a liquid for which the density is selected in such a way that only the red blood cells can cross this barrier during centrifugation, the reaction container being coated in its lower section with an anti-immunoglobulin in order to trap the sensitized red blood cells and to give a characteristic image. Among these techniques, the patent EP 0 058 780 can be cited which discloses a blood phenotyping process in which the reaction mixture is centrifuged through a layer of higher density (a solution of bovine albumin or polyvinyl pyrrolidone), which has the advantage of eliminating the step of washing the sensitized red blood corpuscles. Patent WO 98/02752 can also be cited which discloses a general process for determining the presence of a blood antigen present on erythrocytes or of an antibody binding such an antigen. In this process, the erythrocytes, sensitized or non-sensitized, are separated from the unbound antibodies by centrifugation using a separation medium whose density is greater than that of the liquid containing the antibodies, but less than that of the erythrocytes, the sensitized erythrocytes being separated from the non-sensitized erythrocytes on the lower wall of the reaction container on which an anti-immunoglobulin is immobilized, the non-sensitized erythrocytes being collected at the bottom of the container, the analysis of the final image obtained being specific for the presence or absence of the analyte sought.

Among the variants of the techniques used for phenotyping or for the irregular agglutinin test, those can also be cited which have generally been developed for searching in a sample for an analyte capable of binding to a cell by using magnetic particles, this in particular in order to eliminate centrifugation, an operation necessary in particular in techniques based on agglutination such as the anti-globulin technique (indirect Coombs by agglutination or by immunoadhesion on a solid phase) for the irregular agglutinin test or for phenotyping, or still, as for the irregular agglutinin test, when it is necessary to wash the sensitized red blood cells in order to eliminate the nonspecific antibodies capable of recognizing the anti-immunoglobulin used in the following step.

Indeed, the centrifugation step is always difficult to implement in the methods that are desired to be completely automated, in particular due to the cost of and the space required for the centrifuges, the handling required, etc.

Magnetic particles have long been used for the detection of ligand-receptor or antibody-antigen complexes; for example, methods such as those disclosed in the following patents can be cited:

patent WO 92/17781, which discloses a method tier determining the presence of a ligand in a sample in which magnetic latex particles, capable of being different colors, coated with a substance such as an antibody that is capable of binding with this ligand, are incubated, followed by the application of a magnetic field to the incubation mixture and finally the observation of the presence or absence of agglutination; or patent EP 0,426,170 which discloses a method of determining the presence of a ligand in a sample, a method in which magnetic gelatin particles sensitized with antigens or antibodies capable of binding with this ligand are incubated, followed by the application of a magnetic field to the incubation mixture and finally the observation of the presence or absence of agglutination, the aforementioned method being characterized in that the binding characteristics of these particles are observed after the container, in particular a V-bottomed microplate well, is inclined.

Such magnetic particles have already been used in immunohematology for phenotyping and/or the irregular agglutinin test. Among the documents disclosing such applications, the following can be cited in particular:

patent EP 0,351,857 which discloses an immunological assay method using magnetized markers such as antibodies or antigens bound to magnetic latex beads. These markers are capable of binding to a substance which is sought to be identified in an immunoreaction step, and then the magnetic marker particles are collected on a predetermined area of the surface of a wall in a measurement container using a magnet positioned under this well and under the action of a magnetic field, this process being able to include a substance which can be specifically bound to the substance to be identified immobilized on a predetermined area of the surface of the wall of the measurement container. In particular, an irregular agglutinin test technique by immunoadhesion is disclosed in which erythrocytes bound beforehand at the bottom of a microplate well are then sensitized with the serum of the recipient, then washed (by aspiration and injection of the wash liquid), and then the magnetic latex balls coated with an anti-immunoglobulin are added to said well before the application of a magnetic field;

patent EP 0 528 708 which discloses a method of detection by immunoadhesion of a biological substance likely to be present in a sample. In this method, the erythrocytes to be phenotyped or being used as the screening and/or identification panel are bound beforehand on the bottom of microplate. After sensitizing the erythrocytes thus bound to the test serum (for phenotyping) or to the serum of the recipient to be tested (for the irregular agglutinin test), the wells are washed and then magnetic latex heads coated with anti-immunoglobulin are added. In this method, two types of successive magnetic fields (vertical and circular) are notably implemented in order to displace the magnetic particles that are not specifically bound to the substance being sought; and patent EP 0 230 768 which discloses a method of co-aggregating magnetic particles capable of binding to a substance contained in a sample by means of polycationic or polyanionic compounds in the presence of a magnetic field. This document discloses in particular a method for separating the plasma of a sample of total blood containing red blood cells in which the sample of total blood and a ferrofluid ($FeCl_2/FeCl_3$) coated with succinyl-serum bovine albumin are added sequentially in a container placed on a magnet, the aggregates of particles of erythrocytes thus obtained being pulled towards the magnet thus making it possible to recover the clarified plasma by decantation. Also disclosed in this document is a method making it possible to quantify the presence of an anti-Rh (anti-D) antibody in a sample of plasma prepared according to the preceding method which is incubated in the presence of a suspension of fluorescent Rh+ red blood cells and to which mixture succinyl ferrofluid and polybrene are then sequentially added, the red blood cells being washed several times by the application of a magnetic field and decantation before the addition of an anti-immunoglobulin. The quantification of the anti-Rh antibodies in the plasma sample is evaluated by comparison with controls by analyzing fluctuations in the quantity of fluorescence observed in a given volume.

If these latter techniques using magnetic beads coated with an anti-immunoglobulin or a modified ferrofluid make it possible to avoid centrifugation steps, they do require the use of solid phases coated beforehand with test blood cells or with blood cells to be phenotyped, which are not very stable and must be prepared by the end user. In addition, notably in patent EP 0 230 768, the use of certain magnetic compositions causes the nonspecific co-aggregation of red blood cells after application of the magnetic field, which definitively eliminates the possibility of reading a specific agglutination for the red blood cells in the presence of the erythrocyte anti-antigen antibody, which is the reference technique in the field of blood transfusion.

Thus remains the need for a fast and simple method that can be implemented on a practical and available support such as a microplate, a method in which the centrifugation step is replaced by the application of a magnetic field, which can be entirely automated and which makes it possible to phenotype red blood cells by reading specific agglutination by means of agglutinating test antibodies (test sera) without significantly interfering with the final image obtained, this method also being applicable for the Simonin test (counter-test) within the framework of ABO phenotyping. Such a method would be all the more advantageous if the magnetic composition used does not cause nonspecific aggregation of red blood cells by binding with them after application of the magnetic field and, as the case may be, avoiding the obstruction of the antigenic sites on these red blood cells. This method would be still more advantageous if the magnetic composition used also made it possible in its presence to carry out an immunoadhesion technique of red blood cells on a solid phase, in particular for the irregular agglutinin test and/or the compatibility test, or further for phenotyping requiring the use of non-agglutinating test sera, this without said magnetic composition interfering significantly with the image of the final reaction obtained with this type of technique.

This is precisely the object of the present invention.

The inventors have demonstrated that erythrocytes placed in contact with a diluted, aqueous ferrofluid solution free of surfactants, obtained from a mixture of polyoxoanions of Fe(III) and of at least one M(II) metal of oxidation state II (such as Fe(II)), a ferrofluid such as that obtained in particular by the methods disclosed in examples 1 to 8 of the French patent application published under the number 2 461 521 or in the examples below, and this, contrary to the method disclosed in the patent EP 0 230 768, in the absence of the addition of compounds making it possible to non-specifically bind the magnetic particles of the ferrofluid to the erythrocytes, being not only pulled with the ferrofluid particles to the bottom of the container containing them under the action of a magnetic field induced by a magnet located outside and beneath the aforementioned container, but that moreover this entrainment simultaneously causes the specific agglutination of these erythrocytes when these erythrocytes are also placed in contact with agglutinating anti-antigen blood-group antibodies, of the IgM type, directed against an antigen carried by these erythrocytes.

The inventors have also demonstrated, and in an unexpected way, that the presence of the magnetic particles contained in the solution of ferrofluid thus diluted did not interfere significantly with this specific agglutination, said agglutination being able to be easily demonstrated with the naked eye or by any adequate automated reading system capable of detecting the presence or absence of erythrocyte agglutinates.

The inventors also demonstrated in a surprising way that such a diluted ferrofluid solution no longer interfered significantly with the capacity of the erythrocytes to bind to a solid phase coated with a ligand capable of specifically recognizing a compound bound to the surface of these erythrocytes when the latter are in the presence of magnetic particles contained in this ferrofluid (solid-phase immunoadhesion technique).

Thus, the present invention has as an object a method for phenotyping blood, capable of including the so-called Simonin test, and/or for the search for and/or identification of irregular agglutinins (irregular agglutinin test) in a sample of serum or blood plasma and/or for determining the compatibility between a donor of concentrated erythrocytes and the recipient, characterized in that it includes a step in which the suspension of erythrocytes to be phenotyped or the suspension of test erythrocytes used in this method is placed in contact with an aqueous solution of ferrofluid, preferably without any surfactants, the aforementioned ferrofluid being obtained or likely to be obtained from a mixture of polyoxoanions of Fe(III) and of at least one M(II) metal of oxidation state II (such as Fe(II)), a ferrofluid such as that obtained in particular by the methods disclosed in examples 1 to 8 of the French patent application published under the number 2 461 521 or in the examples below.

In the present description the terms erythrocyte, red blood cell and red blood corpuscle will be employed indifferently to indicate the same blood cell.

Preferably the ferrofluid solution which will be used in the methods of the invention will also result from dilution in an aqueous medium and also preferably in the absence of a surfactant (or detergent) notably to avoid the lysis of the erythrocytes when said erythrocytes are placed in contact with said ferrofluid solution.

By a solution diluted in a surfactant-free aqueous medium of ferrofluid in a surfactant-free aqueous solution, it is hereby specified that the ferrofluid, directly obtained or likely to be directly obtained by the ferrofluid preparation methods disclosed in examples 1 to 8 of the French patent application published under the number 2 461 521 or in the examples below, is a surfactant-free aqueous solution and that the solution used after obtaining this ferrofluid by the aforementioned methods with the purpose of diluting this ferrofluid before its use in the methods of the present invention is also a surfactant-free aqueous solution.

According to a preferred embodiment, the aforementioned ferrofluid solution will be characterized in that it is prepared from a mixture of polyoxoanions of Fe(III) and of at least one M(II) metal of oxidation state II preferably selected among the metals of the first series of transition metals such as Fe(II), Co(II), Mn(II), Cu(II) or Ni(II).

Preferably, the aforementioned ferrofluid solution is characterized in that it is prepared from a mixture of polyoxoanions of Fe(III) and at least one M(II) metal associated with a cation such as $H^+$, $CH_3^+$, $N(CH_3)_4^+$, $N(C_2H_5)_4^+$ or any other cation capable of conferring on the polyoxoanion a greater solubility in water than the cations Na, $K^+$ and $NH_4^+$, these cations could be in particular carried by the appropriate acids, such as HCl, $CH_3COOH$, or by tetramethyl- or tetraethyl-ammonium hydroxide.

Preferably, the aforementioned ferrofluid solution is characterized in that the sources of starting metals chosen for Fe(III) and M(II) for preparing the aforementioned ferrofluid will be the salts chosen among:
for Fe(III), those listed in the French patent application published under the number 2 461 521, page 4, lines 1 and 2, in particular ferric chloride, and
for M(II), those listed in the French patent application published under the number 2 461 521, page 4, lines 3 to 6, in particular ferrous chloride.

Preferably, the aforementioned ferrofluid solution is prepared from a mixture of Fe(III) and the M(II) metal characterized in that the initial molar ratio of oxidation state II is 2±1, in a more preferred way of 2±0.5, 2±0.25 or 2±0.1, an initial molar ratio of 2 between Fe(III) and the M(II) metal of oxidation state II being the most preferred.

Preferably, to the initial mixture of Fe(III) salt and M(II) metal of oxidation state II will be added an appropriate strong base such as sodium hydroxide, tetramethyl- or tetraethyl-ammonium hydroxide.

Preferably, the method according to the invention is characterized in that the aforementioned ferrofluid is obtained by the methods disclosed in examples 1 to 8 of the French patent application published under the number 2 461 521 or by those as described below in the examples.

Preferably still, the method according to the invention is characterized in that the aforementioned aqueous ferrofluid solution is diluted beforehand in a butler or a physiological solution.

In certain applications, in particular when it is a question of improving reaction sensitivity or speed (without, however, increasing the non-specificity of the test), a low ionic strength solution (LISS) buffer can be used.

Those skilled in the art will understand that by buffer or physiological solution is meant a buffer typically used in the field of cellular biology, in particular in immunohematology in order to avoid the lysis of red blood cells. Such buffers or solutions will be, for example, buffers at a physiological pH between 6.8 and 7.5 with the molarity adjusted in such a way that it is similar to the molarity of a 0.9% NaCl solution (approximately 0.15 M NaCl). PBS phosphate buffer at pH 7-7.4, well known to those skilled in the art, can be cited in particular, although in a non-restrictive way.

The composition of LISS buffers will not be developed here, these buffers being well known in immunohematology to encourage agglutination reactions. These buffers are in particular available from immunohematology reagent suppliers (for example, the LISS buffer with the following composition can be cited, although in a non-restrictive way: 16 g/l of glycine, 0.03 M of NaCl and 0.015 M of phosphate at pH 6.7).

According to a preferred embodiment, the method of the invention is characterized in that the aforementioned ferrofluid solution is diluted to between 0.25% and 10% (v/v) in the aforementioned buffer or in the aforementioned physiological solution, preferably between 0.25% and 5%, between 0.25% and 2.5%, between 0.25% and 1%, between 0.25% and 0.75%.

The dilutions between 0.25% and 1%, in particular 0.5%, are particularly preferred for phenotyping by a method of agglutination. It can also be noted that for the compatibility test (determination of direct compatibility between the serum of the recipient and the red blood cell of the donor, see above), dilutions greater than 1%, preferably between 2% and 10%, are also preferred.

For the method according to the invention for the determination of the presence of a blood-group antigen or an anti-antigen blood-group antibody by the erythrocyte agglutination reaction, it is also preferred that the reaction container is a microplate well, preferably a well with a round-shaped or V-shaped bottom.

In the method according to the invention the application of the magnetic field preferably will be obtained by a magnet, of permanent type, located outside and below the reaction container or containers, the aforementioned magnet preferably having a strength between 8,000 and 16,000 gauss, preferably between 10,000 and 14,000 gauss, 12,000 gauss being the preferred strength.

By a method for determining the presence of a blood-group antigen on the surface of an erythrocyte in a sample and, as the case may be, the presence of an anti-antigen blood-group antibody by an erythrocyte agglutination reaction, it is meant to indicate here in a specific way a method for erythrocyte phenotyping (also called here blood or red blood cell phenotyping) corresponding to the search for and the identification of blood-group antigens on the surface of red blood corpuscles (with the exception of the particular ABO system in which, in addition, the presence of the corresponding regular antibodies is sought (so-called Simonin test)), this relating equally to the recipient and the donor.

When the method of the invention relates only to blood phenotyping without the so-called Simonin test for the ABO group, it will be specifically mentioned.

In the present description, an anti-antigen test antibody of a known blood group is intended to indicate polyclonal, monoclonal or recombinant antibodies of known specificity capable of recognizing and binding to the erythrocyte carrying the antigen against which it is directed.

These anti-antigen test antibodies of a known blood group will be able to be provided in liquid form in solution or in desiccated form in the container serving as the support for the agglutination reaction or, as the case may be, in the support being used for the placing in contact of the erythrocytes to be phenotyped with the aforementioned antibody.

Preferably still these antibodies will be of the agglutinating type, such as IgM, in the methods of the invention by an agglutination reaction, that is to say, capable of agglutinating a suspension of erythrocytes carrying the antigen of the group against which the specificity of the aforesaid antibody is directed, this without the assistance of an anti-immunoglobulin and under the appropriate conditions well known to those skilled in the art or indicated on the data sheet provided by the supplier related to the use of such an antibody (such as, for example, in a saline medium at ambient temperature or at 37° C., etc.).

In the methods of phenotyping according to the invention in which it will be preferred or necessary for certain blood-group antigens to carry out phenotyping according to the invention by a solid phase immunoadhesion technique, in particular:

when the aforementioned phenotyping is carried out using a container for the final reaction whose lower internal wall will be coated beforehand with an anti-immunoglobulin or with any ligand capable of specifically recognizing and binding the specific test antibody/erythrocyte complex; or when the aforementioned phenotyping is carried out using a container for the final reaction whose lower internal wall will be coated beforehand with the aforesaid test antibody capable of specifically recognizing and binding the erythrocyte carrying the antigen corresponding to the test antibody, the aforementioned anti-antigen test antibodies of a known blood group could be non-agglutinating in nature, such as IgG or one their fragments capable of recognizing the aforementioned antigen.

According to a first specific aspect, the present invention relates to a method according to the invention for determining, by an erythrocyte agglutination reaction, the presence of a blood-group antigen on the surface of an erythrocyte of a sample and, as the case may be, the presence of an anti-antigen blood-group antibody in a sample, characterized in that it is comprised of the following steps:

a) the mixture, in particular in a glass bottle, of a suspension of erythrocytes contained in the sample, and as the case may be, of a suspension of test erythrocytes of a known group, with a ferrofluid solution so as to obtain a homogeneous suspension of the aforesaid erythrocytes in the ferrofluid solution;

b) the placing in contact in a container of the suspension of erythrocytes obtained in step a) with:
 an anti-antigen test antibody of a known blood group if the suspension obtained in step a) is a suspension of erythrocytes from the sample; and, as the case may be,
 the sample likely to contain an anti-antigen blood-group antibody if the suspension obtained in step a) is a suspension of test erythrocytes of a known blood group,
this step being followed by an incubation step;

c) the shaking of the suspension obtained in step b) after incubation;

d) the application of a magnetic field to said container in such a way that the particles of ferrofluid are pulled to the bottom of the aforesaid container;

e) the shaking of the suspension obtained in step d);

f) the reading by the naked eye and/or by any other suitable reading system of the possible presence of erythrocyte agglutinates in the container.

According to a specific method, the mixture in step a) of the aforesaid method could be carried out before the test, one or several hours in advance, one or several days in advance, or, as the case may be, could be obtained from a supplier, particularly when it is a question of mixing a suspension of test erythrocytes of a known group with a ferrofluid solution. This will be the case for all of the methods, in particular for the irregular agglutinin test in which it will be necessary to mix a suspension of test erythrocytes of a known group with a ferrofluid solution.

According to this method for determining, by an erythrocyte agglutination reaction, the presence of a blood-group antigen or an anti-antigen blood-group antibody according to the invention, the aforementioned ferrofluid solution used in step a) is a diluted ferrofluid solution directly obtained or likely to be directly obtained by the ferrofluid preparation methods disclosed in examples 1 to 8 of the French patent application published under the number 2 461 521 or in the examples below.

According to this method for determining, by an erythrocyte agglutination reaction, the presence of a blood-group antigen or an anti-antigen blood-group antibody according to the invention, it is preferred that before step b), the aforementioned suspension of erythrocytes contained in the sample is subjected beforehand to the action of a protease enzyme.

According to this method for determining, by an erythrocyte agglutination reaction, the presence of a blood-group antigen or an anti-antigen blood-group antibody according to the invention, it is also preferred that when the suspension obtained in step a) is a suspension of erythrocytes from the sample, the aforementioned suspension of erythrocytes is subjected to the action of the protease enzyme at the end of step a).

According to this method for determining, by an erythrocyte agglutination reaction, the presence of a blood-group antigen or an anti-antigen blood-group antibody according to the invention, it is also preferred that in step b), the anti-antigen blood-group test antibodies are contained in desiccated form in the container before the placing in contact of the suspension obtained in step a) if this suspension is a suspension of erythrocytes from the sample.

According to this method for determining, by an erythrocyte agglutination reaction, the presence of a blood-group antigen or an anti-antigen blood-group antibody according to the invention, it is also preferred that the anti-antigen test antibodies of a known blood group or the anti-antigen blood-group antibodies likely to be contained in the sample are agglutinating antibodies, preferably of the IgM type.

According to this method for determining, by an erythrocyte agglutination reaction, the presence of a blood-group antigen or an anti-antigen blood-group antibody according to the invention, it is also preferred that the incubation step at the end of step b) is carried out for a period of time between 5 and 15 minutes, preferably for 10 minutes, at ambient temperature.

According to this method for determining, by an erythrocyte agglutination reaction, the presence of a blood-group antigen or an anti-antigen blood-group antibody according to the invention, it is also preferred that shaking step c) is carried out for a period of time between 30 seconds and 2.5 minutes, preferably between 1 minute and 2 minutes.

According to this method for determining, by an erythrocyte agglutination reaction, the presence of a blood-group antigen or an anti-antigen blood-group antibody according to the invention, it is also preferred that step d), application of a magnetic field to said container, is carried out by means of a magnet located outside and beneath the container in such a way that the particles of ferrofluid are pulled to the bottom of the aforesaid container according to a vertical axis.

According to this method for determining, by an erythrocyte agglutination reaction, the presence of a blood-group antigen or an anti-antigen blood-group antibody according to the invention, it is also preferred that in step d) the aforementioned magnet is a permanent magnet of a strength between 10,000 and 14,000 gauss, preferably 12,000 gauss.

According to this method for determining, by an erythrocyte agglutination reaction, the presence of a blood-group antigen or an anti-antigen blood-group antibody according to the invention, it is also preferred that in step d) the magnetic field is applied to said container for 2.5 minutes to 10 minutes, preferably for 4 minutes to 6 minutes.

According to this method for determining, by an erythrocyte agglutination reaction, the presence of a blood-group antigen or an anti-antigen blood-group antibody according to the invention, it is also preferred that step c), the shaking of the suspension before reading, is carried out in two successive shaking steps, the second being shorter in time and less vigorous than the first.

According to this method for determining, by an erythrocyte agglutination reaction, the presence of a blood-group antigen or an anti-antigen blood-group antibody according to the invention, it is also preferred that in step a) the aforementioned suspension of erythrocytes from erythrocytes contained in the sample results from a pellet of erythrocytes obtained after sedimentation or centrifugation, preferably by sedimentation, of a sample of total blood of an individual.

According to this method for determining, by an erythrocyte agglutination reaction, the presence of a blood-group antigen or an anti-antigen blood-group antibody according to the invention, it is also preferred that in step a) the aforementioned sample likely to contain the anti-antigen blood-group antibodies is a sample of plasma or serum obtained after sedimentation or centrifugation, preferably by sedimentation, of a sample of total blood of an individual.

According to this method for determining, by an erythrocyte agglutination reaction, the presence of a blood-group antigen or an anti-antigen blood-group antibody according to the invention, it is also preferred that in step b) the aforementioned container is a microplate well, preferably a round-bottomed well.

According to this method for determining, by an erythrocyte agglutination reaction, the presence of a blood-group antigen or an anti-antigen blood-group antibody according to the invention, it is also preferred that in step c) shaking is carried out using a microplate shaker at a speed between 500 rpm and 800 rpm, preferably between 650 rpm and 750 rpm.

According to this method for determining, by an erythrocyte agglutination reaction, the presence of a blood-group antigen or an anti-antigen blood-group antibody according to the invention, it is also preferred that in step e) shaking is carried out in 2 steps using a microplate shaker, a first shaking for 1 minute to 2.5 minutes at a speed between 800 rpm and 1000 rpm, preferably 105 seconds at a speed of 900 rpm, and the second shaking for 30 seconds to 1 minute at a speed between 350 rpm and 550 rpm, preferably for 45 seconds at a speed of 450 rpm.

According to this method for determining, by an erythrocyte agglutination reaction, the presence of a blood-group antigen or an anti-antigen blood-group antibody according to the invention, it is also preferred that in step b):
  40 µl to 50 µl of the suspension of erythrocytes obtained in step a) are placed in contact in said well with the anti-antigen test antibodies of a known blood group contained in desiccated form at the bottom of the well, if the suspension of erythrocytes obtained in step a) is a suspension of erythrocytes from the sample; and, as the case may be,
  20 µl to 30 µl of the suspension of erythrocytes obtained in step a) are placed in contact in said well with 20 µl to 30 µl of plasma or of serum of the sample likely to contain the anti-antigen blood-group antibodies, if the suspension of erythrocytes obtained in step a) is a suspension of test erythrocytes of a known blood group.

According to a specific embodiment, the present invention has as an object a method according to the invention for the ABO blood grouping of a sample of total blood from an individual, characterized in that in step b):
  the suspension of erythrocytes from the sample obtained in step a) is placed in distinct containers with an anti-A test antibody and an anti-B test antibody; and
  a sample of plasma or serum from the individual is placed in distinct containers with a suspension of test erythrocytes of group A, preferably A1, a suspension of test erythrocytes of group B, and, as the case may be, a suspension of test erythrocytes of group O,
characterized in that in step f) the possible presence of erythrocyte agglutinates in each of the aforesaid containers is evaluated by reading with the naked eye and/or any other suitable reading system, the whole of these readings making it possible to determine the individual's ABO group.

According to an equally specific embodiment, the present invention has as an object a method according to the invention for blood phenotyping, excluding the Simonin test, of a sample of total blood from an individual, characterized in that in step b):

the suspension of erythrocytes from the sample obtained in step a) is placed in contact in distinct containers with a test antibody specific for the blood-group antigens whose presence or absence on the erythrocytes of the sample is sought to be determined, each container containing only one antibody specificity, characterized in that in step f) the possible presence of erythrocyte agglutinates in each of the aforesaid containers is evaluated by reading with the naked eye and/or any other suitable reading system, the whole of these readings making it possible to determine the phenotype of the individual for the antigens of the blood group sought.

According to an equally specific embodiment, the present invention has as an object a method according to the invention for blood phenotyping, Simonin test included, of a sample of total blood from an individual, characterized in that in step b):

the suspension of erythrocytes from the sample obtained in step a) is placed in contact in distinct containers with an anti-A test antibody and an anti-B test antibody, and the suspension of erythrocytes from the sample obtained in step a) is placed in contact in other distinct containers with a test antibody specific for the blood-group antigen, except antigen A and B, whose presence or absence on the erythrocytes of the sample is sought to be determined, each container containing only one antibody specificity; and a sample of plasma or serum from the individual is placed in contact in other distinct containers with a suspension of test erythrocytes from group A, preferably A1, a suspension of test erythrocytes of group B, and, as the case may be, a suspension of test erythrocytes of group O, characterized in that in step f) the possible presence of erythrocyte agglutinates in each of the aforesaid containers is evaluated by reading with the naked eye and/or any other suitable reading system, the whole of these readings making it possible to determine the ABO group of the individual to determine the phenotype of the individual for the other antigens of the blood group sought.

According to another aspect, the present invention relates to a method according to the invention for the search for and/or the identification of irregular antibodies in a sample of plasma or serum of a recipient, characterized in that it is comprised of the following steps:

a) incubation in a first container of the aforesaid sample of plasma or serum with a suspension of test erythrocytes of known phenotype under conditions allowing the irregular antibodies likely to be present to specifically bind on the test erythrocytes;

b) the addition of a ferrofluid solution to the mixture obtained in step a) so as to obtain a homogeneous suspension of the aforesaid erythrocytes in the ferrofluid solution;

c) the application of a magnetic field to said container by means of a magnet located outside and beneath the aforementioned container so as to pull the aforementioned erythrocytes with the magnetic particles contained in the ferrofluid to the bottom of the aforesaid container (erythrocyte plate), followed, as the case may be, by removal of the supernatant obtained;

d) as the case may be, washing the pellet of erythrocytes and magnetic particles by the addition of a wash solution, followed by the removal of the supernatant after plating the erythrocytes, this step being able to be repeated several times;

e) the transfer into a second container of a sample or of the totality of the suspension of erythrocytes and ferrofluid obtained in step c) or d), said second container being coated on its lower internal wall with an anti-globulin capable of recognizing and binding on this wall the irregular-antibody/test-erythrocyte complexes possibly present;

f) the application of a magnetic field to said second container in such a way that the erythrocytes are pulled to the bottom of the aforesaid container with the magnetic particles contained in the ferrofluid; and g) reading with the naked eye and/or any other suitable reading system of the distribution of the erythrocytes on the lower wall of the container.

According to this method, the presence of a single red point located on the vertical axis of the container and at its bottom could be interpreted as the absence of irregular antibodies.

On the other hand, the significant presence of erythrocytes distributed throughout the area of the container coated with anti-immunoglobulin (or anti-species, see the variant below) could be interpreted as a presence of irregular antibodies.

The invention relates to a method for the search for and/or the identification of irregular antibodies according to the present invention, characterized in that step b), addition of a ferrofluid solution to the suspension of the aforesaid test erythrocytes, is carried out before the addition of the aforesaid sample of serum or plasma.

The invention relates to a method for the search for and/or the identification of irregular antibodies according to the present invention, characterized in that:

before step e), the suspension of washed erythrocytes obtained in the preceding step is placed in contact in the first container with an anti-immunoglobulin solution, and, as the case may be, after shaking and incubation;

a sample or the totality of the suspension of erythrocytes and ferrofluid obtained is transferred into the second container, said second container being coated on its lower internal wall with anti-globulin, preferably an anti-species antibody, capable of recognizing and binding on this wall the anti-immunoglobulin/irregular-antibody/test-erythrocyte complexes possibly present.

According to another aspect, the present invention relates to a method according to the invention for determining the compatibility between an erythrocyte concentrate of a donor and a recipient, characterized in that it is comprised of the steps of the method for the search for and/or the identification of irregular antibodies according to the present invention but in which in step a), a sample of plasma or serum of the recipient is incubated in the aforementioned first container with a suspension of erythrocytes of the donor under conditions allowing the antibodies likely to be present and directed against a blood-group antigen present on the erythrocytes of the donor to bind to the aforementioned erythrocytes, the following steps and their variants being identical to the method for the irregular agglutinin test according to the present invention.

According to another aspect the present invention relates to a device for determining, by an erythrocyte agglutination reaction, the presence of a blood-group antigen on the surface of an erythrocyte of a sample and, as the case may be, the presence of an anti-antigen blood-group antibody in a sample, characterized in that it is comprised of:

a) a container containing a ferrofluid solution;

b) a container containing a suspension of erythrocytes of the sample to be tested;

c) one or more reaction containers containing an anti-antigen blood-group antibody, as the case may be, in desiccated form and, as the case may be, one or more containers containing a suspension of test erythrocytes of a known group;

d) at least one magnet or an assembly of magnets which can be located outside and beneath said container or containers;

e) a shaking system for the aforesaid container or containers, and, as the case may be, f) a reader capable of evaluating the presence of erythrocyte agglutinates in each container.

Preferably, the device according to the invention is characterized in that the aforementioned reaction container is a microplate well, preferably with a round bottom.

According to a specific embodiment, the invention has as an object a device for the ABO blood grouping of a sample of total blood from an individual, characterized in that:

the aforementioned containers containing a suspension of test erythrocytes of a known group distinctly contain a suspension of test erythrocytes of group A, preferably A1, a suspension of test erythrocytes of group B, and, as the case may be, a suspension of test erythrocytes of group O; and the aforementioned containers containing an anti-antigen blood-group antibody distinctly contain an anti-A antibody and an anti-B antibody.

According to an equally specific embodiment, the invention has as an object a device for blood phenotyping, excluding the Simonin test, of a sample of total blood from an individual, characterized in that:

the aforementioned containers distinctly contain a test antibody specific for the blood-group antigens whose presence or absence on the erythrocytes of the sample is sought.

According to another specific embodiment, the invention has as an object a device for blood phenotyping, including the Simonin test, of a sample of total blood from an individual, characterized in that:

the aforementioned containers containing a suspension of test erythrocytes of a known group distinctly contain a suspension of test erythrocytes of group A, preferably A1, a suspension of test erythrocytes of group B, and, as the case may be, a suspension of test erythrocytes of group O; and the aforementioned containers containing an anti-antigen blood-group antibody distinctly contain an anti-A antibody, an anti-B antibody and a test antibody specific for the blood-group antigens, except ABO, whose presence or absence on the erythrocytes of the sample is sought to be determined.

According to another aspect, the present invention has as an object a kit of reagents for determining, by an erythrocyte agglutination reaction, the presence of an antigen of the blood group on the surface of a erythrocyte of a sample and, as the case may be, the presence of an anti-antigen blood-group antibody in a sample, characterized in that it is comprised of:

a) one or more reaction containers distinctly containing an anti-antigen blood-group antibody;

b) a ferrofluid solution, diluted as the case may be in a buffer or in a physiological solution, preferably in a low ionic strength solution buffer;

c) as the case may be, a suspension of test erythrocytes of a known blood group; and e) as the case may be, one or more magnets which can be placed outside and beneath the reaction containers.

The invention particularly relates to a kit of reagents according to the invention, for the ABO blood grouping of a sample of total blood from an individual, characterized in that:

the aforementioned containers containing a suspension of test erythrocytes of a known group distinctly contain a suspension of test erythrocytes of group A, preferably A1, a suspension of test erythrocytes of group B, and, as the case may be, a suspension of test erythrocytes of group O; and the aforementioned containers containing an anti-antigen blood-group antibody distinctly contain an anti-A antibody and an anti-B antibody.

The invention also relates to a kit of reagents according to the invention for blood phenotyping, including the Simonin test, of a sample of total blood from an individual, characterized in that it includes in addition containers distinctly containing test antibodies specific for the blood-group antigens, other than antigen A and B, whose presence or absence on the erythrocytes of the sample to be phenotyped is sought to be determined.

Preferably, the kit of reagents according to the invention is characterized in that the aforementioned anti-antigen blood-group antibodies contained in the aforementioned containers are in desiccated form.

Preferably still, the kit of reagents according to the invention is characterized in that the aforementioned containers are microplate wells, preferably with round bottoms.

The examples which follow are intended to illustrate the invention without limiting its scope in any way.

EXAMPLE 1

Manufacture of Pre-Purified Ferrofluid

Materials and Method
Manufacture of Ferrofluid:
Specific Materials and Chemicals
1 Stericup GS filter, 200 ml, 0.22 µm (ref.: 107943)
1 magnet
28-30% solution of $NH_4OH$ (Acros, ref.: 205840025 batch no. A017559001)
60% solution of $HNO_3$ (Normapur, ref.: UN 2031 batch no. N182)
$FeCl_2, 4H_2O$ (Sigma, ref.: 22,029-9 hatch no. S18641-463)
$FeCl_3, 6H_2O$ (Sigma, ref.: F-2877, batch no. 033K0108).
Manufacture of Ferrofluid:
Preparation:

1) Weigh 13.51 g of $FeCl_3$ and dissolve in 20 ml of filtered demineralized water by magnetic stirring. Transfer the solution to a 50 ml test tube, rinse and bring up to 50 ml with filtered demineralized water (solution at 1 M).

2) Weigh 19.88 g of $FeCl_2$ and dissolve in 20 ml of filtered demineralized water by magnetic stirring. Transfer the solution to a 50 ml test tube, rinse and bring up to 50 ml with filtered demineralized water (solution at 2 M).

3) Filter each solution on a 0.22 µm syringe filter.

4) Place 30 ml of a 28% ammonia ($NH_4OH$) solution in a 250 ml test tube and bring up to 120 ml with filtered demineralized water (solution at 2 M).

5) Weigh an empty Rotavapor 1 liter glass flask.
Incubation:

6) Place 10 ml of the $FeCl_2$ solution (2 M) and 40 ml of the $FeCl_3$ solution (1 M) in the 1 liter Rotavapor flask, homogenize the solution by shaking the flask by hand.

7) Add 200 ml of filtered demineralized water, homogenize the solution by shaking the flask by hand.

8) Place the flask on an incline in a Rotavapor-type apparatus.

9) Turn the flask at maximum speed to homogenize the solution well.

10) Add 120 ml of the 2 M ammonia solution.
11) Allow the flask to turn for 15 minutes.
12) Place 105 ml of 60% nitric acid ($HNO_3$) in a 1 liter flask and bring up to 1 liter with filtered demineralized water (solution at 1 M).
13) After 15 minutes of rotation, place the flask on the magnet for 4 minutes.
14) Aspirate the totality of the supernatant.
15) Resuspend the pellet.
First Washing:
16) Place the flask on the Rotavapor and turn it at maximum speed.
17) Add 200 ml of the 1 M $HNO_3$ solution.
18) Allow the flask to turn for 10 minutes.
19) Resuspend the pellet.
20) Repeat the operation until the pellet is completely dissolved.
21) Place the flask on the Rotavapor in order to decant the iron suspension.
22) Aspirate the supernatant.
23) Resuspend the pellet.
Steps 16 to 23 can be repeated if necessary.
Final Dilution:
26) Weigh the flask.
27) Deduce the weight of the pellet obtained and calculate the reaction yield:
(Weight of the pellet obtained/Weight of the initial iron)×100
Weight of the initial iron=14.77 g
Yield>55%
28) Add 200 ml of filtered water to the flask.
29) Place the flask on the Rotavapor.
30) Resuspend the pellet.
31) Filter the solution on a 0.22 μm Stericup filter.
Preparation of the Ferrofluid Stock Solution:
Dilute the ferrofluid thus obtained in a LISS buffer or a physiological solution to the desired concentration in a bottle. On a label affixed to the bottle, note the ferrofluid concentration, batch number and manufacture date.
Store the ferrofluid and/or the diluted solution at 4° C.

EXAMPLE 2

Phenotyping of 288 Samples: 144 Donors+144 Recipients by an Automated Technique (on a TECAN Automated System)

TECAN automated system equipped with a plate of 96 unipolar magnets alternating in the North-South direction (12,000 gauss), a Variomag Teleshake (H+P Lab) and a microplate reader.
Blood samples in an EDTA anticoagulant
  extemporaneously placed in contact with the red blood cells (RBC) of patients with various batches of ferrofluid diluted to between 0.3% and 0.5% (v/v) in LISS or in a physiological buffer.
Counter-test: Red blood corpuscles A1 and B of a panel extemporaneously placed in contact with various hatches of ferrofluid diluted to between 0.3% and 0.5% (v/v) in LISS or in a physiological buffer, and stored at 4° C. in 1% RBC (v/v).
5 minutes of magnetization.
Shaking on the Teleshake:
  Before magnetization: 1.5 minutes at 700 rpm NWSE.
  After magnetization: 2 minutes at 900 rpm NWSE+45 seconds at 450 rpm NWSE.

Results:
The performance of the test was evaluated in comparison with a selected reference technique called DUO MICRO in the technical manual.
Use of 4 batches of ferrofluid diluted to between 0.34% and 0.45% (v/v) in LISS or in a physiological buffer prepared as above, assigned randomly to the 288 samples.
Agreement with the reference technique greater than or equal to 98% (6 rejections).
21 Kell positives expected=>20 Kell positives found.
No sedimentation point.
Table comparing the two techniques:

|  |  | Technique with ferrofluid | | | |
|---|---|---|---|---|---|
|  |  | + | − | Uncertain | |
| Duo-Micro | + | 282 | 0 | 0 | 282 |
|  | − | 0 | 0 | 4 (TN; D) | 4 |
|  | Uncertain | 0 | 1 (K in DP) | 1 (C in DP) | 2 |
|  |  | 282 | 1 | 5 | 288 |

Identification of the rejections observed:
  A sample with uncertain Rh1 (reader value=33) and its granular TN (reader value=3).
  A sample with uncertain Rh1 (reader value=28).
  A sample with a double population (DP) weak in C, not detected on the automated system (reader value=6).
  A sample with granular Rh1 (reader value=15).
  A sample with a double population weak in Kell and not detected on the automated system.
  A sample with granular TN (reader value=17).
  It should be noted that the tubes with the double populations contained a very small globular pellet, which could cause sampling problems in the tube with the TECAN needles.
  Moreover, the double populations were only very weakly detected by the reference technique (Duo Micro by centrifugation), with the naked eye and the reader interpreting them as uncertain.
  The granulations are only very slightly visible with the naked eye and if the negativity threshold is raised they will no longer be detected by the reader.

EXAMPLE 3

Sample Phenotyping: Automated Technique (on a TECAN Automated System)

Materials:
  Samples from donors and recipients in EDTA (ethylenediaminetetraacetic acid) tubes.
  Washed pure ferrofluid solutions
    extemporaneously placed in contact with the red blood cells (RBC) of patients with various batches of ferrofluid diluted to between 0.3% and 0.5% (v/v) in LISS.
  Counter-test red blood corpuscles extemporaneously placed in contact and preferably stored in 1% physiological buffer at 4° C.
  Bromelain (Diagast code no. 69024).
  Duo Micro microplates, batch 302000.
  LISS (Diagast code V6901B-1).
  Greiner 96-well plate (Deep Well, 700 μl).
Protocol:
  Centrifuge the tubes from the patients at 2,500 G for 5 minutes at ambient temperature.

Place the sample tubes in the sample racks.
Place the tubes of test red blood corpuscle (A1 and B) in suspension in the ferrofluid for the counter-test in a sample rack.
Make a magnetizing ferrofluid solution with an OD at 450 nm equivalent to 0.9 in LISS, to be distributed into 8 hemolysis tubes in position 1 to 8, grid no. 4.
Fill rack no. 2 with bromelain.
Place the Deep Well plate on site no. 1, grid no. 7, and the Duo Micro microplates on sites no. 2 and 3, grid no 7.
Begin the Duo Micro protocol with the TECAN:
  deposit 25 μl of plasma in the counter-test wells,
  in the Deep Well, distribute 240 μl of magnetizing solution per sample to be tested,
  add 10 μl of the globular pellet to the magnetizing solution,
  homogenize the globular suspension by aspirating and injecting several times,
  add 700 μl of bromelain,
  deposit 40 μl of the magnetized globular suspension and bromelain in the wells of the 2 Duo Micro microplates,
  deposit 25 μl of test red blood corpuscles in the counter-test wells,
  incubate the microplates for 10 minutes,
  shake the microplates on the Teleshake at 700 rpm for 1.5 minutes,
  magnetize the microplates for 5 minutes,
  shake the microplates on the Teleshake at 900 rpm for 2 minutes, then at 450 rpm for 45 seconds.
Read the plate on the reader, then read with the naked eye.

EXAMPLE 4

Phenotyping of 312 Samples Using a Manual Technique

Protocol:
Manufacture of Ferrofluid: See Example 1.
Manual feasibility carried out on 312 samples: 160 donors+ 152 recipients.
  Blood samples in EDTA.
  Extemporaneous magnetizing of the RBC of patients with various batches of ferrofluid stock solution diluted in LISS in order to have a final ferrofluid dilution of between 0.3% and 0.5%.
  Counter-test: red blood corpuscles A1 and B of a panel placed in suspension in a glass bottle in the diluted ferrofluid solution (stock solution diluted to 0.3% in LISS or in a physiological buffer) and stored at 4° C. in 1% RBC (in LISS, preferably in a physiological buffer).
  Magnetize for 5 minutes.
  Shake on the Teleshake:
    before magnetization: 1.5 minutes at 700 rpm NWSE,
    after magnetization: 2 minutes at 900 rpm NWSE+45 seconds at 450 rpm NWSE.
Results:
  The performance of the test was evaluated in, comparison with a selected reference technique called DUO MICRO in the technical manual.
  Use of the 4 batches of ferrofluid cited above assigned randomly to the 312 samples.
  Agreement with the reference technique—98%.
  Rejection=2% (7 of 312 samples rejected).
  35 Kell positives expected=>34 Kell positives found.
  Sedimentation point %—0.4% (15 of 3744 wells).

Table Comparing the Two Techniques:

|  |  | Ferrofluid technique | | | |
| --- | --- | --- | --- | --- | --- |
|  |  | + | − | Uncertain | |
| Duo-Micro | + | 305 | 0 | 0 | 305 |
|  | − | 0 | 0 | 5 (TN = granulations) | 5 |
|  | Uncertain | 0 | 1 (Kell in DP) | 1 (C in DP) | 2 |
|  |  | 305 | 1 | 6 | 312 |

Identification of the Rejections Observed:
  A sample with a double population (DP) low in C, interpreted as uncertain (reader value=33) but also interpreted as uncertain with the naked eye and with the reader in the reference technique (reader value=27).
  A sample with a double population in Kell and undetected (FN). It should be noted that the sample has very little volume in the tube, which makes the sampling of the pellet very difficult and can lead to a decrease in the hematocrit in this step of the protocol.
  5 samples had granulations in the TN (reader values=18, 14, 12, 36 and 18) as well as in all the specificities for which they were negative (the reader values were less than 20). Two of these samples were on the same plate.

CONCLUSION

At the end of this study, we can see that the performance of the technique using ferrofluid for phenotyping is very close to that of the reference technique used in comparison.

If the "ferrofluid" technique did not detect certain very low double populations, whereas the reference technique detected them as uncertain, it can be noted nevertheless that these 2 false negatives can be explained by the fact that the sample tubes were only slightly filled and that the volume of the globular pellet was low, thus the hematocrit of the sample was too low.

In general, and for the entire population of recipients tested, 30% were samples with double populations which were always detected by the "ferrofluid" technique.

With regard to the samples rejected following granulations, these are slightly visible with the naked eye and the reader rejects them because they exceed the negativity threshold set at 10. Currently this threshold of negativity is set at 15 or even 20 on all readers. If we were to set the threshold at these same values the rejection rate would be less than 1%.

The invention claimed is:
1. A method of phenotyping blood, capable of including the so-called Simonin test, and/or for searching for irregular agglutinins (irregular agglutinin test) in a sample of serum or blood plasma and/or for determining the compatibility between a donor of concentrated erythrocytes and the recipient, characterized in that it includes a step in which the suspension of erythrocytes to be phenotyped or the suspension of test erythrocytes used in this method is placed in contact with an aqueous solution of ferrofluid obtained from a mixture of polyoxoanions of Fe(III) and of at least one M(II) metal of oxidation state II.

2. A method according to claim 1, characterized in that the aforementioned aqueous ferrofluid solution is surfactant-free.

3. A method according to claim 1 or claim 2, characterized in that the aforementioned ferrofluid is prepared from a mixture of polyoxoanions of Fe(III) and of at least one M(II) metal of oxidation state II selected among the metals of the first series of transition metals.

4. A method according to one of the claims 1 to 3, characterized in that the aforementioned ferrofluid is prepared from a mixture of polyoxoanions of Fe(III) and Fe(II).

5. A method according to one of the claims 1 to 4, characterized in that the aforementioned ferrofluid is prepared from the aforesaid mixture of polyoxoanions associated with a cation.

6. A method according to claim 5, characterized in that the aforementioned cation is selected among $H^+$, $CH_3^+$, $N(CH_3)_4^+$, $N(C_2H_5)_4^+$.

7. A method according to one of the claims 1 to 6, characterized in that the sources of starting metals chosen for Fe(III) and M(II) for preparing the aforementioned ferrofluid will be ferric chloride and ferrous chloride, respectively.

8. A method according to one of the claims 1 to 7, characterized in that the aforementioned ferrofluid is prepared from an initial mixture of Fe(III) and of M(II) metal of a molar ratio between 1 and 3.

9. A method according to claims 1 to 8, characterized in that the aforementioned ferrofluid is prepared from an initial mixture of Fe(III) and of M(II) metal of a molar ratio equal to 2±0.1.

10. A method according to claim 1, characterized in that the aforementioned ferrofluid is obtained by a process for obtaining ferrofluids in an aqueous medium without the addition of surfactants to prepare them, said process comprising the following steps:
   i) adding to a base, a suitable amount of the product of dissolution in water of the salts of the appropriate metals, to form a gel;
   ii) effecting a cation exchange by means of an aqueous solution of a suitable cation; and
   iii) separating the gel so obtained which is then solubilized to an aqueous solution.

11. A method according to one of the claims 1 to 10, characterized in that the aforementioned aqueous ferrofluid solution is diluted beforehand in a buffer or in a physiological solution.

12. A method according to one of the claims 1 to 10, characterized in that the aforementioned aqueous ferrofluid solution is diluted to between 0.25% and 10% (v/v) in the aforementioned buffer or in the aforementioned physiological solution.

13. A method according either to claim 11 and claim 12, characterized in that the aforementioned buffer is a low ionic strength solution buffer.

14. A method according to one of the claims 1 to 13 for determining, by an erythrocyte agglutination reaction, the presence of a blood-group antigen on the surface of an erythrocyte of a sample, characterized in that it is comprised of the following steps:
   a) mixing a suspension of erythrocytes contained in the sample, and as the case may be, of a suspension of test erythrocytes of a known group, with a ferrofluid solution so as to obtain a homogeneous suspension of the aforesaid erythrocytes in the ferrofluid solution;
   b) placing in contact in a container of the suspension of erythrocytes obtained in step a) with: an anti-antigen test antibody of a known blood group if the suspension obtained in step a) is a suspension of erythrocytes from the sample; and, as the case may be, the sample likely to contain an anti-antigen blood-group antibody if the suspension obtained in step a) is a suspension of test erythrocytes of a known blood group, this step being followed by an incubation step;
   c) shaking of the suspension obtained in step b) after incubation;
   d) application of a magnetic field to said container in such a way that the particles of ferrofluid are pulled to the bottom of the aforesaid container;
   e) shaking of the suspension obtained in step d);
   f) reading by the naked eye and/or by any other suitable reading system of the possible presence of erythrocyte agglutinates in the container.

15. A method according to claim 14, characterized in that in step a), the aforementioned ferrofluid solution is a ferrofluid solution obtained from a mixture of polyoxoanions of Fe(III) and of at least one M(II) metal of oxidation state II which was diluted beforehand in a buffer or in a physiological solution in a range between 0.2% and 2% (v/v).

16. A method according to claim 15, characterized in that the aforementioned ferrofluid solution obtained from a mixture of polyoxoanions of Fe(III) and of at least one M(II) metal of oxidation state II was diluted beforehand in a buffer or a physiological solution in a range between 0.25% and 0.75% (v/v), preferably 0.5%.

17. A method according to one of the claims 13 to 16, characterized in that before step b), the aforementioned suspension of erythrocytes contained in the sample is subjected beforehand to the action of a protease enzyme, preferably bromelain.

18. A method according to claim 17, characterized in that when the suspension obtained in step a) is a suspension of erythrocytes from the sample, the aforementioned suspension of erythrocytes is subjected to the action of the protease enzyme at the end of step a).

19. A method according to one of the claims 13 to 18, characterized in that in step b), the anti-antigen blood-group test antibodies are contained in desiccated form in the container before the placing in contact of the suspension obtained in step a) if this suspension is a suspension of erythrocytes from the sample.

20. A method according to one of the claims 13 to 19, characterized in that the anti-antigen test antibodies of a known blood group or the anti-antigen blood-group antibodies likely to be contained in the sample are agglutinating antibodies, preferably of the IgM type.

21. A method according to one of the claims 13 to 20, characterized in that the incubation step at the end of step b) is carried out for a period of time between 5 and 15 minutes, preferably for 10 minutes at ambient temperature.

22. A method according to one of the claims 13 to 21, characterized in that shaking step c) is carried out for a period of time between 30 seconds and 25 minutes, preferably between 1 minute and 2 minutes.

23. A method according to one of the claims 13 to 22, characterized in that step d), application of a magnetic field to said container, is carried out by means of a magnet located outside and beneath the container in such a way that the particles of ferrofluid are pulled to the bottom of the aforesaid container according to a vertical axis.

24. A method according to claim 23, characterized in that in step d) the aforementioned magnet is a permanent magnet of a strength between 10,000 and 14,000 gauss, preferably 12,000 gauss.

25. A method according to claim 23 or claim 24, characterized in that in step d) the magnetic field is applied to said container for 2.5 minutes to 10 minutes, preferably for 4 minutes to 6 minutes.

26. A method according to one of the claims 13 to 25, characterized in that step e), the shaking of the suspension before reading, is carried out in two successive shaking steps, the second being shorter in time and less vigorous than the first.

27. A method according to one of the claims 13 to 26, characterized in that in step a) the aforementioned suspension of erythrocytes from erythrocytes contained in the sample results from a pellet of erythrocytes obtained after sedimentation of a sample of total blood of an individual.

28. A method according to one of the claims 13 to 27, characterized in that in step a) the aforementioned sample likely to contain the anti-antigen blood-group antibodies is a sample of plasma or serum obtained after sedimentation of a sample of total blood of an individual.

29. A method according to one of the claims 13 to 28, characterized in that in step b) the aforementioned container is a microplate well, preferably a round-bottomed well.

30. A method according to claim 29, characterized in that in step c) shaking is carried out using a microplate shaker at a speed between 500 rpm and 800 rpm, preferably between 650 rpm and 750 rpm.

31. A method according to claim 29 or claim 30, characterized in that in step e) shaking is carried out in 2 steps using a microplate shaker, a first shaking for 1 minute to 2.5 minutes at a speed between 800 rpm and 1000 rpm, preferably 105 seconds at a speed of 900 rpm, and the second shaking for 30 seconds to 1 minute at a speed between 350 rpm and 550 rpm, preferably for 45 seconds at a speed of 450 rpm.

32. A method according to one of the claims 29 to 31, characterized in that in step b):
 40 μl to 50 μl of the suspension of erythrocytes obtained in step a) are placed in contact in said well with the anti-antigen test antibodies of a known blood group contained in desiccated form at the bottom of the well, if the suspension of erythrocytes obtained in step a) is a suspension of erythrocytes from the sample; and, as the case may be,
 20 μl to 30 μl of the suspension of erythrocytes obtained in step a) are placed in contact in said well with 20 μl to 30 μl of plasma or of serum of the sample likely to contain the anti-antigen blood-group antibodies, if the suspension of erythrocytes obtained in step a) is a suspension of test erythrocytes of a known blood group.

33. A method according to one of the claims 13 to 32 for the ABO blood grouping of a sample of total blood from an individual, characterized in that in step b):
 the suspension of erythrocytes from the sample obtained in step a) is placed in distinct containers with an anti-A test antibody and an anti-B test antibody; and
 a sample of plasma or serum from the individual is placed in distinct containers with a suspension of test erythrocytes of group A, preferably A1, a suspension of test erythrocytes of group B, and, as the case may be, a suspension of test erythrocytes of group O,
 characterized in that in step f) the possible presence of erythrocyte agglutinates in each of the aforesaid containers is evaluated by reading with the naked eye and/or any other suitable reading system, the whole of these readings making it possible to determine the individual's ABO group.

34. A method according to one of the claims 13 to 33 for blood phenotyping, excluding the Simonin test, of a sample of total blood from an individual, characterized in that in step b):
 the suspension of erythrocytes from the sample obtained in step a) is placed in contact in distinct containers with a test antibody specific for the blood-group antigens whose presence or absence on the erythrocytes of the sample is sought to be determined, each container containing only one antibody specificity,
 characterized in that in step f) the possible presence of erythrocyte agglutinates in each of the aforesaid containers is evaluated by reading with the naked eye and/or any other suitable reading system, the whole of these readings making it possible to determine the phenotype of the individual for the antigens of the blood group sought.

35. A method according to one of the claims 13 to 33 for blood phenotyping, Simonin test included, of a sample of total blood from an individual, characterized in that in step b):
 the suspension of erythrocytes from the sample obtained in step a) is placed in contact in distinct containers with an anti-A test antibody and an anti-B test antibody, and
 the suspension of erythrocytes from the sample obtained in step a) is placed in contact in other distinct containers with a test antibody specific for the blood-group antigen, except antigen A and B, whose presence or absence on the erythrocytes of the sample is sought to be determined, each container containing only one antibody specificity; and
 a sample of plasma or serum from the individual is placed in contact in other distinct containers with a suspension of test erythrocytes from group A, preferably A1, a suspension of test erythrocytes of group B, and, as the case may be, a suspension of test erythrocytes of group O,
 characterized in that in step f) the possible presence of erythrocyte agglutinates in each of the aforesaid containers is evaluated by reading with the naked eye and/or any other suitable reading system, the whole of these readings making it possible to determine the ABO group of the individual to determine the phenotype of the individual for the other antigens of the blood group sought.

36. A method according to one of the claims 3 to 13 for the search for and/or the identification of irregular antibodies in a sample of plasma or serum of a recipient, characterized in that it is comprised of the following steps:
 a) incubation in a first container of the aforesaid sample of plasma or serum with a suspension of test erythrocytes of known phenotype under conditions allowing the irregular antibodies likely to be present to specifically bind on the test erythrocytes;
 b) the addition of a ferrofluid solution to the mixture obtained in step a) so as to obtain a homogeneous suspension of the aforesaid erythrocytes in the ferrofluid solution;
 c) the application of a magnetic field to said container by means of a magnet located outside and beneath the aforementioned container so as to pull the aforementioned erythrocytes with the magnetic particles contained in the ferrofluid to the bottom of the aforesaid container (erythrocyte plate);
 d) the transfer into a second container of a sample or of the totality of the suspension of erythrocytes and ferrofluid obtained in step c), said second container being coated on its lower internal wall with an anti-globulin capable of recognizing and binding on this wall the irregular-antibody/test-erythrocyte complexes possibly present;
 e) the application of a magnetic field to said second container in such a way that the erythrocytes are pulled to the bottom of the aforesaid container with the magnetic particles contained in the ferrofluid; and
 f) reading with the naked eye and/or any other suitable reading system of the distribution of the erythrocytes on the lower wall of the container.

37. A method according to claim 36, characterized in that step b), addition of a ferrofluid solution to the suspension of the aforesaid test erythrocytes, is carried out before the addition of the aforesaid sample of serum or plasma.

38. A method according to claim 36, characterized in that, after step c), the process comprises a step of washing the pellet of erythrocytes and magnetic particles by the addition of a wash solution, followed by the removal of the supernatant after plating the erythrocytes, this step being able to be repeated several times.

39. A method according to one of the claims 3 to 13, for determining the compatibility between an erythrocyte concentrate of a donor and a recipient, characterized in that it is comprised of the steps of the method for the search for and/or the identification of irregular antibodies according to one of the claims 36 to 38 but in which method in step a),
   a sample of plasma or serum of the recipient is incubated in the aforementioned first container with a suspension of erythrocytes of the donor under conditions allowing the antibodies likely to be present and directed against a blood-group antigen present on the erythrocytes of the donor to bind to the aforementioned erythrocytes,
   the following steps being identical.

40. A method according to claim 3, characterized in that said M(II) metal of oxidation state II is selected among the group consisting of: Fe(II), Co(II), Mn(II), Cu(II) and Ni(II).

41. A method according to claim 14 for determining, by an erythrocyte agglutination reaction, the presence of a blood-group antigen on the surface of an erythrocyte of a sample and the presence of an anti-antigen blood-group antibody in a sample.

42. A method according to claim 36, characterized in that, in step c), the application of a magnetic field to said container by means of a magnet located outside and beneath the aforementioned container is followed by removal of the supernatant obtained.

43. A method according to claim 38, characterized in that:
   before step d), the suspension of washed erythrocytes obtained in the preceding step is placed in contact in the first container with an anti-immunoglobulin solution; and
   a sample or the totality of the suspension of erythrocytes and ferrofluid obtained is transferred into the second container, said second container being coated on its lower internal wall with anti-globulin, preferably an anti-species antibody, capable of recognizing and binding on this wall the anti-immunoglobulin/irregular-antibody/test-erythrocyte complexes possibly present.

44. A method according to claim 43, characterized in that, before step d), the suspension of washed erythrocytes obtained in the preceding step is placed in contact in the first container with an anti-immunoglobulin solution, and, after shaking and incubation a sample or the totality of the suspension of erythrocytes and ferrofluid obtained is transferred into said second container.

45. A method according to claim 10, characterized in that in step i) said salts of the appropriate metals are salts of Fe(III) and salts of a bivalent metal M(II).

* * * * *